United States Patent [19]

Lafon

[11] Patent Number: 4,603,019

[45] Date of Patent: Jul. 29, 1986

[54] N-(METHOXYPHENACYL)-AMINE DERIVATIVES

[75] Inventor: Louis Lafon, Paris, France

[73] Assignee: Laboratoire L. Lafon, Paris, France

[21] Appl. No.: 674,298

[22] Filed: Nov. 23, 1984

[30] Foreign Application Priority Data

Nov. 25, 1983 [FR] France .................................. 83 18868

[51] Int. Cl.[4] ..................... C07C 95/08; C07C 143/00
[52] U.S. Cl. ............................. 260/501.19; 564/342; 564/343; 564/344; 564/357; 564/365
[58] Field of Search ....................... 564/342, 343, 344; 260/501.17, 501.19

[56] References Cited

U.S. PATENT DOCUMENTS

| | | | |
|---|---|---|---|
| 1,680,055 | 8/1928 | Legerlotz | 564/344 X |
| 2,606,208 | 8/1952 | Burtner | 564/342 |
| 3,225,096 | 12/1965 | Mills et al. | 564/342 X |
| 3,317,604 | 5/1967 | Baltzly et al. | 564/344 |
| 3,492,351 | 1/1970 | Koppe et al. | 564/344 |
| 3,873,539 | 3/1975 | Houlihan et al. | 564/344 X |
| 3,895,030 | 7/1975 | Lafon | 564/344 X |

OTHER PUBLICATIONS

Moed et al., "Chemical Abstracts", vol. 49, pp. 12357–12358 (1955).

Primary Examiner—Robert V. Hines
Attorney, Agent, or Firm—McDougall, Hersh & Scott

[57] ABSTRACT

This invention relates to new N-(methoxyphenacyl)-amine derivatives selected from the group consisting of (i) the N-(methoxyphenacyl)-alkylamines of the general formula

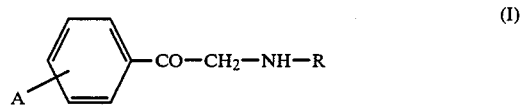

(I)

wherein A is $OCH_3$, and R is $C_3$–$C_8$-alkyl or $C_3$–$C_8$-hydroxyalkyl; and,
(ii) addition salts thereof.

These new derivatives are useful as pharmaceuticals, in particular as peripheral vasodilating agents.

Their method of preparation is based upon the following reaction scheme

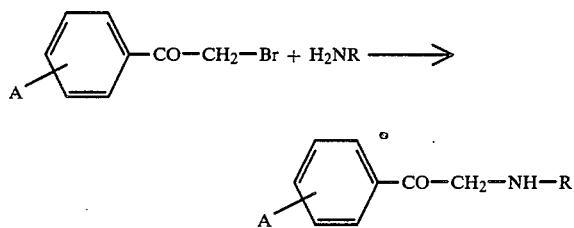

3 Claims, No Drawings

N-(METHOXYPHENACYL)-AMINE DERIVATIVES

This invention is concerned with N-(methoxyphenacyl)-amine derivatives as new industrial products. It is also concerned with the method of preparation of these new derivatives which are useful as pharmaceuticals, on the one hand, and as intermediate compounds in the synthesis of 2-alkylamino-1-(methoxyphenyl)-1-ethanol derivatives (which are also useful as pharmaceuticals), on the other hand.

The new compounds according to the invention which belong to the family of the N-(methoxyphenacyl)-amine derivatives are characterized in that they are selected from the group consisting of (i) the N-(methoxyphenacyl)-alkylamines of the general formula

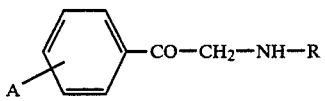

(I)

wherein A is $OCH_3$ group, and R is a $C_3$-$C_8$-alkyl group or a $C_3$-$C_8$-hydroxyalkyl group; and, (ii) addition salts thereof.

The expression "addition salts" is understood here as meaning firstly the acid addition salts obtained by reacting the free base of the formula I with inorganic or organic acids, and secondly the ammonium salts. Hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular among the acids which can be used to salify the base of the formula I. Halides such as $CH_3I$ and $CH_3Cl$ may be mentioned in particular among the compounds making it possible to obtain ammonium salts. In general terms, the acid addition salts are preferred to the ammonium salts.

The preferred alkyl and hydroxyalkyl groups which are included within the scope of the definition of the R radical are branched hydrocarbon radicals (which comprises advantageously from 4 to 6 carbon atoms), such as in particular $C(CH_3)_3$, $CH(CH_3)CH(CH_3)_2$, $CH(CH_3)CH_2CH(CH_3)_2$, $CH[CH(CH_3)_2]_2$, $C(CH_3)_2CH_2C(CH_3)_3$, $C(CH_3)_2CH_2OH$, $CH(CH_3)_2$.

A number of compounds according to the invention have been collated in Table I below without in any way implying a limitation.

The compounds which are preferred according to the invention in view of their pharmacological properties are characterized in that they are selected from the group consisting of (a) the N-(3-methoxyphenacyl)-tertiobutylamine methanesulfonate,
(b) the N-(4-methoxyphenacyl)-1,3-dimethylbutylamine and its addition salts,
(c) the N-(2-methoxyphenacyl)-tertiobutylamine and its addition salts, and,
(d) the N-(4-methoxyphenacyl)-N-2-(2-hydroxymethylpropyl)-amine and its addition salts.

TABLE I

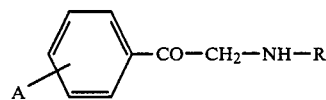

| Product | Code No | A | R |
|---|---|---|---|
| Example 1 (a) | CRL 40833 | 3-$OCH_3$ | $C(CH_3)_3$ |
| Example 2 (b) | CRL 40799 | 4-$OCH_3$ | $CH(CH_3)CH_2CH(CH_3)_2$ |
| Example 3 (b) | CRL 40818 | 2-$OCH_3$ | $C(CH_3)_3$ |
| Example 4 (b) | CRL 40798A | 4-$OCH_3$ | $C(CH_3)_2CH_2OH$ |
| Example 5 (b) | CRL 40833A | 3-$OCH_3$ | $C(CH_3)_3$ |
| Example 6 (c) | — | 3-$OCH_3$ | $C(CH_3)_2CH_2C(CH_3)_3$ |
| Example 7 (b) | — | 3-$OCH_3$ | $CH[CH(CH_3)_2]_2$ |
| Example 8 (b) | — | 2-$OCH_3$ | $CH(CH_3)CH_2CH(CH_3)_2$ |

Notes
(a) methanesulfonate
(b) hydrochloride
(c) hemifumarate

Compounds of the formula I can be prepared according to a method known per se by use of classical reaction mechanisms. The method which is recommended here comprises reacting a methoxyphenacyl bromide of the formula

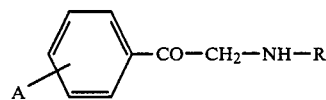

(II)

(wherein A is $OCH_3$) with an alkylamine of the formula $H_2NR$   (III)

(wherein R is defined as indicated above), in the presence of an inert solvent selected in particular from the group consisting of $C_1$-$C_2$-alcohols, chloroform, dioxan, tetrahydrofuran and mixtures thereof, for 0.25 h to 2 h at a temperature comprised between room temperature (15°–20° C.) and the reflux temperature of the reaction medium, whereby at least 3 mols of III are used for 1 mol of II.

Compounds of the formula I are used as intermediate products in the synthesis of 2-alkylamino-1-(methoxyphenyl)-1-ethanol derivatives of formula IV according to the following reaction mechanism (wherein A and R are defined as indicated above). The compounds of formula IV are useful as pharmaceuticals as indicated in French patent application No. 83 18869 of the Applicant and filed on Nov. 25, 1983.

The compounds according to the invention exhibit beneficial effects on the central nervous system (CNS) and, above all, on the cardiovascular system. They possess the common properties to decrease aggressiveness, on one hand, and to act as peripheral vasodilating substances, on the other hand.

According to the invention a therapeutical composition is provided which comprises, in association with a physiologically acceptable excipient, at least a compound of formula I or one of its non-toxic addition salts, as active ingredient.

Of course in a composition of this type, the active ingredient is present in a pharmaceutically effective amount.

Further advantages and characteristics of the invention will be understood more clearly on reading the following description of preparative examples and results of neuropsychopharmacological tests. These elements as a whole do not imply a limitation but are given by way of illustration.

PREPARATION I

Obtention of N-(3-methoxyphenacyl)-tertiobutylamine methanesulfonate, alternative nomenclature: (3-methoxyphenyl)(tertiobutylaminomethyl)-keton methanesulfonate.

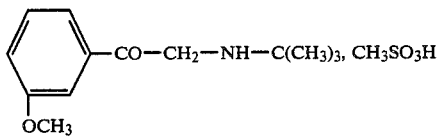

(Example 1; Code No: CRL 40 833)

In chloroform 50 g (0.218 mol) of 3-methoxyphenacyl bromide are dissolved, then the resulting solution is poured into a solution of 79.6 g (1.09 mol; 114 ml) of tertiobutylamine in 100 ml of $CH_3OH$. The reaction medium is heated at the reflux temperature for 2 h, evaporated to dryness, the evaporation residue is taken up with water, extracted with ether, and the ether phase is washed with water then dried over $MgSO_4$. The expected salt is precipitated by means of 21 g of methanesulfonic acid. By recrystallisation from an acetone-ethanol (1:1) v/v mixture, 10 g (yield: 16%) of CRL 40 833 are obtained. M.P.=200° C.

PREPARATION II

Obtention of N-(4-methoxyphenacyl)-1,3-dimethylbutylamine hydrochloride

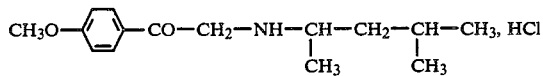

(Example 2; Code No: CRL 40 799)

At room temperature (15°-20° C.) a mixture of 110 g (1.09 mol) of 1,3-dimethylbutylamine, 50 g (0.218 mol) of 4-methoxyphenacyl bromide, 100 ml of $CH_3OH$ and 200 ml of $CHCl_3$ is stirred for 2 hours. Said mixture is heated for 0.25 h at reflux temperature then cooled. After evaporation to dryness, taking up the evaporation residue with 500 ml of $H_2O$ and extraction with ether, the ether phase is extracted with a mixture of 500 ml of water and 50 ml of concentrated hydrochloric acid ($d=1.19$ g/cm$^3$). The aqueous phase is washed with ether and alcalinized with $K_2CO_3$ up to PH11. After extraction with ether, the ether phase is washed with $H_2O$, dried over $MgSO_4$ and filtered. From the filtrate the expected salt is precipitated by addition of a 31 ml solution of HCl 7N in ethanol. By recrystallization from an acetone-methanol (1:1) v/v mixture, 17.8 g (yield: 28%) of CRL 40 799 are obtained. M.P.=190° C. (with decomposition).

Analysis { % N theoretical = 4.90%
          % N measured = 4.90%

PREPARATION III

Obtention of N-(2-methoxyphenacyl)-tertiobutylamine hydrochloride (Example 3; Code No: 40 818)

50 g (0.218 mol) of 2-methoxyphenacyl bromide are dissolved in 250 ml of $CHCl_3$. This solution is poured dropwise into a solution of 79.57 g (1.09 mol; 114 ml) of tertiobutylamine in 100 ml of methanol. The resulting reacting medium is heated to reflux temperature for 2 hours then evaporated to dryness. The evaporation residue is taken up with water, and after extraction with ether, the expected hydrochloride is precipitated by means of ethanol containing hydrochloric acid. By recrystallization from an acetone-methanol (1:1) v/v mixture, 45 g (yield: 80%) of CRL 40 818 are obtained. M.P.=264° C. (with decomposition).

Analysis { % N theoretical = 5.38%
          % N measured = 5.43%

PREPARATION IV

Obtention of N-(4-methoxyphenacyl)-N-2-(2-hydroxymethylpropyl)-amine hydrochloride.

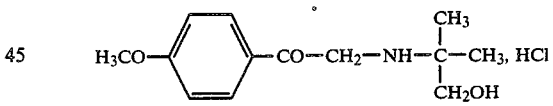

(Example 4; Code No: 40 798A)

A solution of 50 g (0.218 mol) of 4-methoxyphenacyl bromide in 200 ml of chloroform is poured into a solution of 77.6 g (0.872 mol) of 2-(2-hydroxymethylpropyl)-amine in 100 ml of methanol. The reaction mixture is heated for 2 hours at the reflux temperature, then cooled and evaporated to dryness. The evaporation residue is taken up with 500 ml of water and extraction is carried out with ethyl acetate. The ester phase is washed with water and extracted with a mixture of 500 ml of water and 22 ml of concentrated hydrochloric acid ($d=1.19$). The aqueous phase is washed with $CH_3CO_2C_2H_5$ and alcalinized up to pH 11 with $K_2CO_3$. After extraction with $CH_3CO_2C_2H_5$, washing with water, drying over $MgSO_4$ and filtration, the filtrate is precipitated by addition of ethanol containing hydrochloric acid to give the expected CRL 40 798A.

Results of assays which have been carried out with the compounds according to the invention are summed up hereinafter.

A-TOXICITY

The LD-0 (maximum non-lethal dose) per I.P. route in male mice is, for CRL 40 833 (example 1), higher than 256 mg/kg and lower than 450 mg/kg.

The LD-60 per I.P. route in male mice are of the order of 500 mg/kg for 40 833, of 200 mg/kg for CRL 40 799 (example 2) and of 250 mg/kg for CRL 40 818 (example 3).

B-NEUROPSYCHOPHARMACOLOGICAL STUDY

On male mice per I.P. route it is observed that with respect to motility, CRL 40 833 (from the dose of 8 mg/kg) and CRL 40 818 (from the dose of 64 mg/kg) present an increased motility and reactivity, while CRL 40 799 has no effect on motility; moreover CRL 40 833 and CRL 40 799 do not cause, unlike CRL 40 818, a distinct resumption of the motor activity of mice accustomed to their enclosure, do not improve the motor recovery in mice whose motility has been depressed by a brief period in a reduced-pressure enclosure [hypobaric anoxia: pressure reduction of 600 mmHg (i.e. about $8 \times 10^4$ pascals) in 90 seconds; release of vacuum in 45 seconds], and do not change the time taken for convulsions and death to occur following asphyxiant anoxia caused by a curarizing agent (gallamine triiodoethylate) in mice;

with respect to intergroup aggressiveness, CRL 40 833 (at the dose of 32 mg/kg), CRL 40 799 (at the dose of 32 mg/kg) and CRL 40 818 (from the dose of 16 mg/kg) reduce the number of fights in male mice; and, with respect to interactions with reserpine and oxotremorine, the compounds according to the invention slightly oppose the hypothermia induced by reserpine and by oxotremorine.

C-CARDIOVASCULAR STUDY

In a general manner the compounds according to the invention essentially react as peripheral vasodilating substances, the more active ones being the CRL 40 833 and CRL 40 818, the preferred compound on a therapeutical point of view being the CRL 40 833.

(1°) IN ANESTHETIZED DOGS

(a) By intraduodenal route

The assays carried out with a batch of 4 dogs anesthetized with nembutal and receiving by intraduodenal administration doses from 0.08 to 8 mg/kg of CRL 40 833 point out that the flow rate through the femoral artery increases: the minimal active dose is about 0.4 mg/kg and the doses which produce the maximal effect are those comprised between 0.8 and 2 mg/kg [in average the femoral flow rate starting from 86 ml/min. reaches 156 ml/min. (i.e. +81%), the effect duration being from 2 h to more than 3 h];

the flow rate through the vertebral artery increases: the minimal active dose is about 0.4. mg/kg, and the dose which causes the maximal effect is 0.8 mg/kg [in average the vertebral flow rate starting from 51 ml/min. reaches 83 ml/min. (i.e. +57%), the effect duration being of 1-3 h];

the heart beat (i.e. cardiac frequency) increases from the dose of 0.4 mg/kg, then quickly reaches its maximal value [the starting heart beat being of 197 beats/minute, and the maximal value of 217 beats/min.; such a moderate tachycardia is generally present during the whole assay duration].

(b) By intravenous route

CRL 40 833 is administered to two nembutal-anesthetized dogs at the doses of 0.5 and 1 mg/kg I.V.

At the dose of 0.5 mg/kg on a dog (weight: 20 kg) the CRL 40 833 increases the femoral flow rate from 87 to 137 ml/min. (i.e. a variation of +57%) in 1 h [after 3 h, the femoral flow rate being of 110 ml/min. (i.e. a variation of 26% with respect to the same animal before administration of the product to be tested)];

the vertebral flow rate from 25 to 55 ml/min. (i.e. +120%) in 0.25 h [after 3 h, the vertebral flow rate being of 40 ml/min. (i.e. a variation of 60%)];

the heart beat from 180 to 225 beats/min. (i.e. a variation of +25%) in 0,5 h [after 3 h the heart beat being of 210 beats/min. (i.e. a variation of 16%), the arterial pressure being not modified.].

A supplemental dose of 0.5 mg/kg per I.V. route causes an increase of the femoral flow rate to 122 ml/min. (i.e. a variation of +40%), said increase disappearing in 1.5 h;

an increase of the vertebral flow rate to 45 ml/min. (i.e. a variation of +80%) for about 1.5 h, and an increase of the heart beat to 230 beats/min. (i.e. a variation of +27%), the arterial pressure being not modified.

At the dose of 1 mg/kg I.V. on the second dog (weight: 13.5 kg) CRL 40 833 causes the femoral flow rate to increase from 110 to 150 ml/min. (i.e. a variation of +36%) in 0.25 h (the effect during more than 5 h);

the vertebral flow rate to increase from 12 to 37 ml/min. (i.e. a variation of +208%) in 0.25 h (the effect reaching then a stabilisation at 24 ml/min.- i.e. a variation of +100%-for 5 h); and, the heart rate to increase from 150 to 195 beats/min. (i.e. a variation of +16%) after 5 h, the arterial pressure being not modified.

(c) By administration through the femoral artery

The product is perfused through the femoral artery of one leg in 0.5 h to a dog (11 kg) at 0.1 mg/kg then 0.5 mg/kg and to two dogs (12 kg and respectively 13 kg) at 1 mg/kg then 1 mg/kg. It is observed that CRL 40 833 causes a femoral vasodilating action on the non-perfused leg from the dose of 0.6 mg/kg, and leads to a vertebral vasodilation, a tachycardia and, on both femoral arteries an anti-isoprenaline effect.

In particular the femoral flow rate in the non-perfused leg increases from 40 ml/min. to 80 ml/min. after administration of 0.1 mg/kg+0.5 mg/kg, and in average from 120 ml/min. to 152 ml/min. after administration of 1 mg/kg+1 mg/kg. Meanwhile the vertebral flow rates increases from 25 ml/min. to 90 ml/min. after administration of 0.1 mg/kg+0.5 mg/kg, and the heart beat increases from 180 to 220 beats/min. after administration of 0.1 mg/kg+0.5 mg/kg, and in average from 162 to 195 beats/min. after administration of 1 mg/kg+1 mg/kg.

(2°) IN AWAKE DOGS

(a) By I.V. route

Two Labrador dogs accustomed to stay quiet on operation table, receive each successive doses of 0.01, 0.03, 0.1, 0.3 and 1 mg/kg I.V. of CRL 40 833, in order to determine the dose which increases the heart beat of 50 beats/min. and the one which increases the heart beat of 100 beats/min.:

ED-50 beats=0.33 mg/kg
ED-100 beats=1 mg/kg

(b) By oral route

Two other Labrador dogs receive each a sole dose of 1 mg/kg per os of CRL 40 833. It is observed that at the dose of 1 mg/kg P.O. CRL 40 833 causes a reduction of the arterial pressure of 28% (from 128 to 100 mmHg) and an increase of the heart beat of 98% (from 94 to 187 beats/min.) in 1 hour. Then these effects diminish. After 24 h the heart beat is reduced to the control value while the arterial pressure is still 14% lower than the control one.

(3°) GUINEA PIG TRACHEA

The CRL 40 833 is studied by comparaison with isoprenaline on 6 isolated guinea pig trachea subjected to contraction with carbachol ($3 \times 10^{-7}$M). The specific activity, $\alpha$, of CRL 40 833 (that is to say its maximal action with respect to the isoprenaline maximal action taken as the unit) is measured. The $pD_2$ value (which measures the affinity of the agonist for the receptor) and the $CE_{50}$ (concentration giving 50% of the maximal effect obtained with the substance to be tested) are calculated. The results of these assays are given in Table II hereinafter.

TABLE II

| | ISOLATED GUINEA PIG TRACHEA | |
|---|---|---|
| Parameters | Isoprenaline | CRL 40 833 |
| $\alpha$ | 1 | 0.84 |
| $pD_2$ | 6.85 ± 0.064 | 4.11 ± 0.107 |
| $CE_{50}$ | $1.48 \times 10^{-7}$ M | $8.5 \times 10^{-5}$ M (a) |

Note
(a) which corresponds to a $CE_{50}$ CRL 40 833/$CE_{50}$ isoprenaline ratio of 574

The conclusions drawn from the data of Table II is that CRL 40 833 was shown to exhibit beneficially a $\beta_2$+ effect which is 574 times lower than the isoprenaline one.

Moreover assays performed per os on genetically hypertensive rats confirm the interest of CRL 40 833 as peripheral vasodilating agent.

In clinical assays, CRL 40 833 was shown to give good results as vasodilating agent, in particular by oral administration to adults at a daily rate of 3 to 4 gelatine capsules (each containing 50 mg of CRL 40 833).

What is claimed is:

1. A pharmacologically effective N-(methoxyphenacyl)-amine derivative having vasodilating action, the derivative selected from the group consisting of
   (i) N-(3-methoxyphenacyl)-tertiarybutylamine,
   (ii) N-(4-methoxyphenacyl)-1,3-dimethylbutylamine,
   (iii) N-(2-methoxyphenacyl)-tertiarybutylamine,
   (iv) N-(4-methoxyphenacyl)-N-2-(2-hydroxymethylpropyl)-amine, and
   (v) addition salts thereof.

2. The derivative of claim 1 consisting of N-(3-methoxylphenacyl)-tertiarybutylamine methanesulfonate.

3. A therapeutical composition comprising, in association with a physiologically acceptable excipient, a pharmaceutically effective amount of a N-(methoxyphenacyl)-amine derivative according to claim 1.

* * * * *

UNITED STATES PATENT AND TRADEMARK OFFICE
CERTIFICATE OF CORRECTION

PATENT NO. : 4,603,019
DATED : July 29, 1986
INVENTOR(S) : Louis Lafon

It is certified that error appears in the above-identified patent and that said Letters Patent is hereby corrected as shown below:

In column 2, line 47 "C." should read -- c --.

In column 4, line 2 "PH" should read -- pH --; line 24 "reacting" should read -- reaction --.

In column 6, line 18 "of 60%" should read -- of + 60% --; line 44 "heart rate" should read -- heart beat --.

Signed and Sealed this

Fourteenth Day of October, 1986

[SEAL]

Attest:

DONALD J. QUIGG

Attesting Officer

Commissioner of Patents and Trademarks